United States Patent
Bardani

(10) Patent No.: US 6,478,790 B2
(45) Date of Patent: Nov. 12, 2002

(54) IMPLANT DEVICE AND DOSAGE FORM EMPLOYABLE THEREIN

(76) Inventor: Frank M. Bardani, 8 Ponds La., Purchase, NY (US) 10577

(*) Notice: Subject to any disclaimer, the term of this patent is extended or adjusted under 35 U.S.C. 154(b) by 88 days.

(21) Appl. No.: 09/742,635

(22) Filed: Dec. 22, 2000

(65) Prior Publication Data

US 2002/0082565 A1 Jun. 27, 2002

(51) Int. Cl.[7] ............................................. A61M 5/00
(52) U.S. Cl. .................. 604/891.1; 604/60; 424/423
(58) Field of Search ............................... 604/891.1, 64, 604/60, 59, 239, 187, 181, 93.01; 424/423, 422

(56) References Cited

U.S. PATENT DOCUMENTS 3,921,632 A * 11/1975 Bardani ...................... 424/423
4,444,335 A * 4/1984 Wood et al. ................. 222/309
6,197,324 B1 * 3/2001 Crittenden ................... 424/423

* cited by examiner

Primary Examiner—Gene Mancene
Assistant Examiner—Arnold Castro
(74) Attorney, Agent, or Firm—Morton S. Simon

(57) ABSTRACT

An implant device comprises a tubular member having a bore, a charging end and a pointed elongated annular concavely beveled implanting end. A rod is removably insertable within the bore for delivery of an implant dosage form charged within the bore. A stop member for hindering movement of the rod sufficiently to prevent unintentional delivery of the implant dosage form but not sufficient to prevent same when delivery is intended is mounted on the tubular member. A truncated cylindrical solid shaped implant dosage form having an ellipsoidal face is positioned in the bore at the implanting end in alignment with same so that a substantially continuous elipsoidal surface is presented.

12 Claims, 2 Drawing Sheets

IMPLANT DEVICE AND DOSAGE FORM EMPLOYABLE THEREIN

FIELD OF THE INVENTION

The present invention relates to an improved device for the administration of drugs. More particularly, the invention relates to an improved device for subcutaneous introduction of drug implants and to a novel shaped implant dosage form for use in such device.

BACKGROUND OF THE INVENTION

Techniques and devices for introducing solid medicaments beneath the skin are known in the art. Medical use of drug implants was initiated as early as 1861, see Howard Jones, N., J. Hist. Med. 2, 201 (1947).

Implants have advantageously been used for administration of hormones, such as testosterone, estradiol and other drugs, where slow, constant release and continuous absorption of a drug over prolonged time periods is desired. The long lasting effect of a drug implant frees the patient from the need to take multiple periodic parenteral or oral doses. In the long run, implant therapy is often more economical. Moreover, where a dosage regimen is critical, use of implants eliminates the possibility of missed doses. Though clinical use of pellet implants has declined with the development of oral dosage forms, it nevertheless remains a valuable medical tool in, for example, drug absorption studies. Surface area of an implant is readily determined and controlled. Moreover, the effective area of a pellet in contact with body tissues can be measured, before and after implantation, by simple direct inspection of the implant.

As stated heretofore, devices for subcutaneous introduction of implants are disclosed in the prior art. One such device comprises an injector needle, having a central longitudinal axial bore and a sharp beveled end, a first plunger having a sharp beveled end and a second plunger having a blunt end. The first plunger and the second plunger are each removably insertable within the bore of the injector needle. The technique employed with this prior art device is as follows:

The area wherein the pellet is to be inserted is anesthetized with a local anesthetic. A small incision is made in the skin to permit free passage of the injector needle. The first plunger is inserted into the bore of the injector needle, then the injector needle, with the first plunger in place, is inserted into the subcutaneous tissue. When insertion of the injector needle is complete the first plunger is withdrawn from the bore. A drug pellet is then introduced into the injector bore and gently forced down the bore and into the subcutaneous tissues with the blunt end of the second plunger. Once the pellet is fully inserted, the injector and the second plunger seated in the bore are simultaneously withdrawn. The incision is then closed with sutures, a clip, or an adhesive bridge etc.

The aforementioned prior art device suffers from several major defects and has not proven successful. Firstly, a preliminary surgical incision is required before the device can be employed. Secondly, if upon insertion into the subcutaneous tissues, the injector needle, with the first plunger in place, is not properly oriented, that is to say, the beveled sharp end of the first plunger is not in alignment with the beveled sharp end of the injector needle, insertion of the device will result in considerable tearing of the tissues.

U.S. Pat. No. 3,921,632 discloses an improvement over the above-described prior art device. Use of such improved device obviates the need for preliminary surgical incision. The device of such patent makes a clean incision. No stitching or sutures are generally thereafter required. Furthermore, in the device of such patent, means are provided for preventing improper orientation of the sharp end of the injector needle and the sharp end of the first plunger so that disadvantageous tearing of the skin and tissues is avoided.

The device of U.S. Pat. No. 3,921,632 comprises: a tubular member having a central longitudinal axial bore therethrough, a pointed elongated annular concavely beveled implanting end and a charging end. The implanting and charging ends communicate with the bore. A first plunger having a solid pointed elongated annular concavely beveled end is adapted to be removably inserted in the bore for slidable movement therein. When the first plunger is completely inserted in the bore of the tubular member the beveled implanting end of the tubular member and the beveled end of the first plunger are aligned to form a complimentary substantially continuous, pointed, elongated, annular concavely beveled penetration surface. The first plunger is slidably moveable in the bore of the tubular member from a first to a second position at which insertion of the plunger in the bore is complete. Means are also provided for permitting the alignment at only the second position. As is shown in FIG. 4 of the patent, a second plunger having a blunt tip is also provided. The device of U.S. Pat. No. 3,921,632 works as follows:

As is seen from FIG. 1 of the patent, the first plunger 6 is introduced into the bore of the tubular member and when fully introduced the ends (elements 9, 3, and 10) are in alignment. This is more clearly shown in FIG. 2 of the patent. The cannula of the device is then injected into the patient. After it is introduced the first plunger is slidably removed from the bore and a pellet implant is inserted into the bore. The blunt ended plunger is then employed to push the pellet through the bore and into the subcutaneous tissues of the patient.

SUMMARY OF THE INVENTION

The present invention presents improvements on the above-described device of U.S. Pat. No. 3,921,632.

The implant device of the present invention can advantageously be made of metal, such as stainless steel, or of plastic and stainless steel and can be sterilized by steam or radiation. Most desirably, with the exception of the cannula, all parts are made of plastic so that the device is less costly and disposable.

A further advantage of the improved device of the present invention is that it contains fewer parts than the device of U.S. Pat. No. 3,921,632. There is no need for the blunt plunger 16 of such patent. Moreover, the device of the present invention can be preloaded with one or more pellet implants. This is possible because of the novel form of the solid dosage form of the present implant device.

As will be more fully described later on in this disclosure, the present invention provides a solid implant dosage form that is shaped so that when it is in the bore of the injector needle and positioned at its end, a face of the solid dosage form aligns with the beveled end of the injector needle so as to present a complimentary elongated annular concave surface

DESCRIPTION OF THE DRAWINGS

The present invention will now be described in greater detail with reference to the accompanying drawings in which like elements are assigned the same numerical designation.

In the drawings.

DETAILED DESCRIPTION OF THE INVENTION

Figure 1:
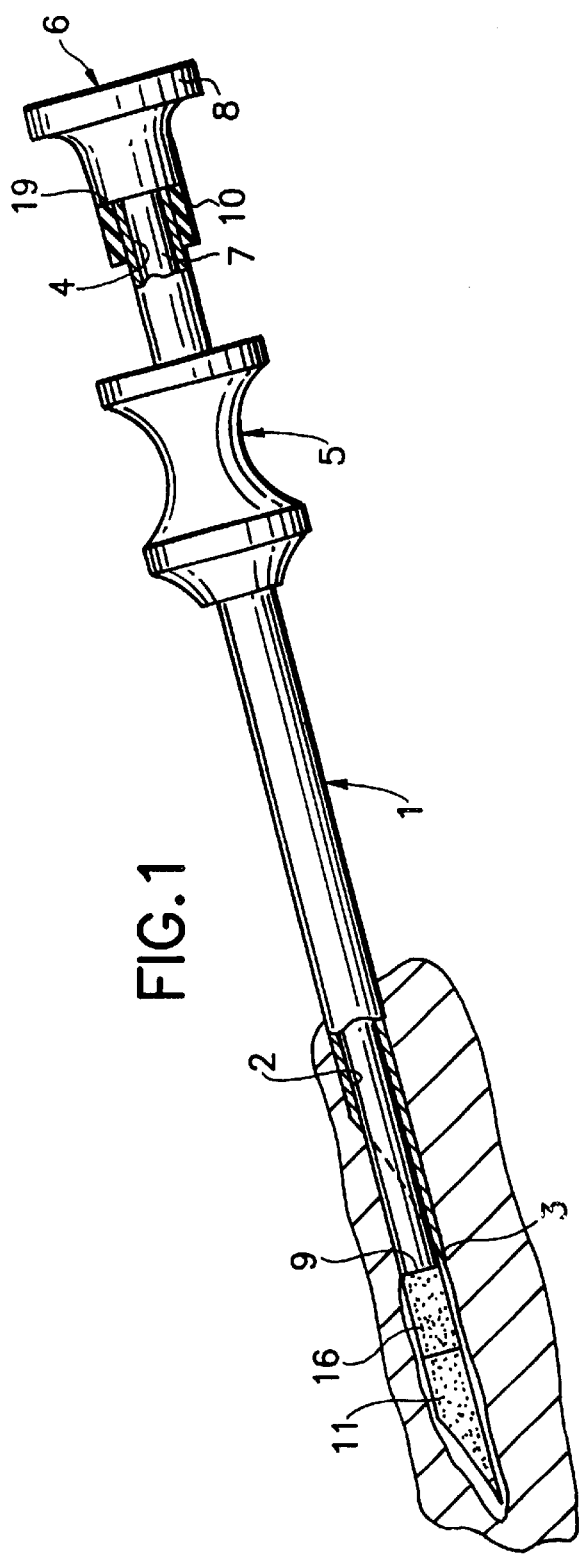
FIG. 1 is a plan view of a preferred embodiment of an implant device in accordance with the present invention, partly in section and showing delivery of two implant dosage forms.

Referring now to FIG. 1: Injector cannula or tubular member 1 has a longitudinal axial bore 2 therethrough, a pointed elongated annular concavely beveled implanting end 3 and a charging or inlet end 4. Bore 2 communicates with implanting end 3 and with inlet end 4. A finger hold 5, which can also serve as insertion limiting stop member, is mounted on tubular member 1.

Finger hold 5 can be hourglass shaped so as to provide a convenient gripping surface for the fingers. Finger hold 5 can be fixed in position on or unitary with tubular member 1. Alternatively, finger hold 5 can be adjustable in position along the longitudinal axis of tubular member 1 so as to permit regulation of the maximum depth of penetration of implanting end 3 into the subcutaneous tissues. Adjustability of the position of finger hold 5 on tubular member 1 can be attained by providing finger hold 5 with releasable friction gripping means. For example, finger hold 5 can have a bore that has internal threading. A setscrew having external complementary threading is positioned within the bore. The set screw can be threaded downwards and into contact with the outer surface of tubular member 1 to frictionally engage same and fix the position of finger hold 5 thereon. Alternatively, finger hold 5 can be internally threaded and tubular member 1 can have complimentary external threading that permit finger hold 5 to be threaded towards or away from implanting end 3. Means for enabling adjustability of the position of finger hold 5 on tubular member 1 are disclosed in U.S. Pat. No. 3,921,632 and are incorporated herein by reference.

Figure 2:
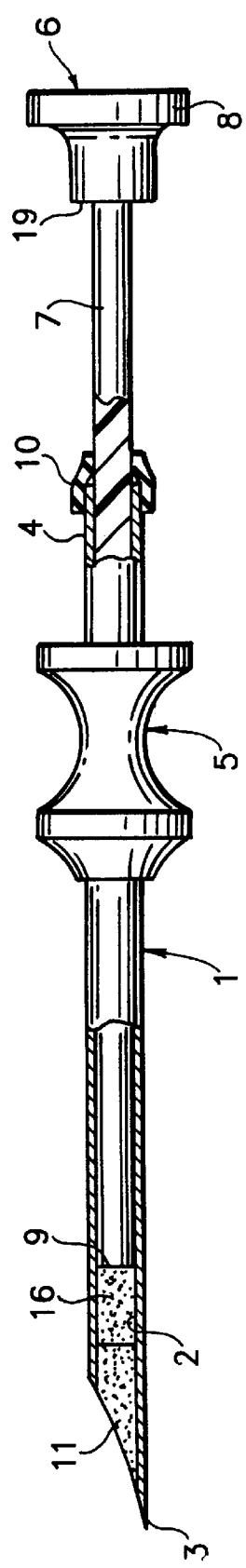
FIG. 2 is plan view of the implant device of FIG. 1, partly in section, showing the device preloaded and prior to use.

As illustrated in FIGS. 1 and 2, a plunger 6, comprised of a solid rod portion 7, a head portion 8, the difference between the diameter of the rod portion 7 and the head portion 8 defining a shoulder 19, and a blunt end 9 is removably insertable in bore 2 of tubular member 1 for slidable movement therein along the longitudinal axis of tubular member 1.

Figure 3:
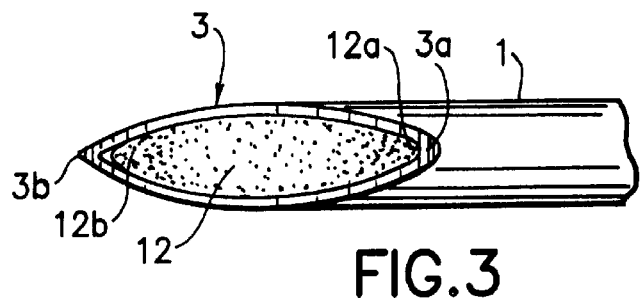
FIG. 3 is a partial top view of the implanting end of the tubular member of the device of FIGS. 1 and 2, showing an implant in the bore of the tubular member.

As more fully shown in FIG. 3, implanting end 3 of tubular member 1 is beveled and pointed in order to facilitate penetration into the subcutaneous tissues for delivery of one or more implant dosage forms.

As shown in FIGS. 1 and 2, the device of the present invention can be preloaded with one or more implant dosage forms. The implant dosage forms are loaded into bore 2 at charging or inlet end 4. To facilitate introduction of the implant dosage form(s) into bore 2, inlet end 4 can be configured as described in U.S. Pat. No. 3,921,632. Plunger 6 is then introduced into bore 2 and slid downwardly therein, until blunt end 9 is in contact with the pellet(s) within bore 2.

Preferably, as shown in FIGS. 1 and 2, a stop member 10 is mounted on tubular member 1. Stop member 10 functions to hinder downward movement of plunger 6 into the bore 2. The resistance provided by stop member 10 should be sufficient to prevent unintentional ejection of the implant dosage form(s) contained in bore 2. It should not, however, be so high as to prevent an intentional downward movement of plunger 6 when the device is used to inject the implant dosage form(s). Basically, the stop member 10 functions to prevent accidental premature delivery of the implant dosage form(s) from the device.

As seen in FIG. 2, prior to use of the preloaded device, the stop member 10 is preferably mounted on the tubular member at the inlet end 4 and in contact with rod 7. Alternatively, stop member 10 can be mounted on rod 7 and in contact with inlet end 4 of tubular member 1.

As is shown in the preferred embodiment of FIGS. 1 and 2, stop member 10 frictionally engages both tubular member 1 and rod 7.

FIG. 2 shows the preferred embodiment of the device of the present invention prior to use. Stop member 10 is adapted to provide sufficient frictional resistance against downward movement of rod 7 within bore 2 towards implanting end 3 so as to prevent unintentional delivery of the implant dosage form(s). The frictional resistance provided by stop member 10 should be such as to be readily overcome when the device is intentionally used to subcutaneously deliver its preloaded implant dosage form(s).

FIG. 1 shows the device of the invention after it has been employed to subcutaneously deliver the implant dosage forms. It should be noted that rod 7 is fully inserted in bore 2 and stop member 10 is positioned on tubular member 1 and only in contact with shoulder 19 of head portion 8 of plunger 6.

Stop member 10 can be a rubber or plastic ring circumferentially mounted on the tubular member 1. Stop member 10 is preferably frictionally fit on tubular member 1 so that slideable motion of the plunger 6 into bore 2 occurs only when sufficient force is applied to head portion 8 to overcome the frictional resistance.

As noted earlier, when preloaded with one or more implant dosage forms and fitted as shown in FIG. 1, the device of the present invention can be packaged and sterilized by methods well known to those skilled in the art.

As shown in FIGS. 1, 2, 3 and 4, the solid implant dosage form 11, positioned in bore 2 adjacent to the pointed elongated annular concavely beveled implanting end 3, is substantially wedge shaped at one end. Shaped implant 11 has a pointed elongated annular concave beveled face 12 which aligns with the pointed beveled implanting end 3 of the tubular member 1 when the shaped implant dosage form 11 is within bore 2 and adjacent to pointed implanting end 3. When so positioned within bore 2, face 12 and the pointed elongated annular concave beveled implanting end 3 are aligned. Preferably, the alignment produces a substantially continuous surface, which substantially,prevents tearing of tissue when the device is employed to inject the implant dosage form(s). More specifically, when face 12 and implanting end 3 are aligned apexes 12a and 12b are respectively aligned with apexes 3a and 3b of implanting end 3 so as to present a complimentary elongated annular concave surface.

Figure 4:
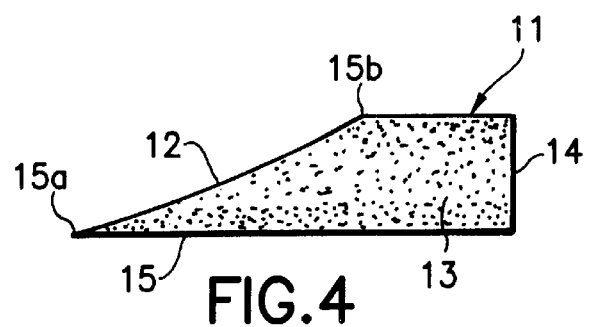
FIG. 4 is a side view of the novel shaped implant dosage form of the invention that is positioned in the bore of the tubular member adjacent the end of same as is shown in FIG. 2.

The novel implant dosage form 11 of the present invention is preferably cylindrical in shape. As is shown in FIG. 4, implant dosage form 11 has a cylindrical body 13 having a substantially flat bottom 14 and an angularly truncated top portion 15 which slopes downwards from a first point 15a, at an apex at the top of the cylinder wall, to a second point 15b, on the cylinder wall opposite to and closer to bottom 14 and lower than first point 15a. Ellipsoidal face 12 extends between the first and second points. Thus the novel implant dosage form 13 of the instant invention has a substantially wedge shaped top and a substantially flat bottom.

If more than one implant dosage form is to be injected, only the implant dosage form that is within bore 2 and adjacent end 3 must have an elongated annular concave face 12 as heretofore described. In other words, the first implant dosage form within the bore 2 and adjacent implanting end 3 must be the shaped implant dosage form 11. Other implant dosage form(s) 16 positioned in bore 2 upstream from shaped implant dosage form 11 can possess any convenient shape consistent with the shape of the bore 2 and blunt end 9 of rod 7.

The diameter of the cylindrical implant dosage form of the present invention is limited by the inside diameter of the bore 2 of tubular member 1. Generally, the implant dosage form of the invention has a diameter of from about 1/32 inch to about 1/4 inch and a length of from about 1/8-inch to about 2 inches.

It should be appreciated that when more than one implant dosage form is to be injected each can contain the same medication, in the same or different dose or release rate. The implant dosage forms can also differ in the medication(s) they contain and in the dose or release rate of each such medication.

Figure 5:
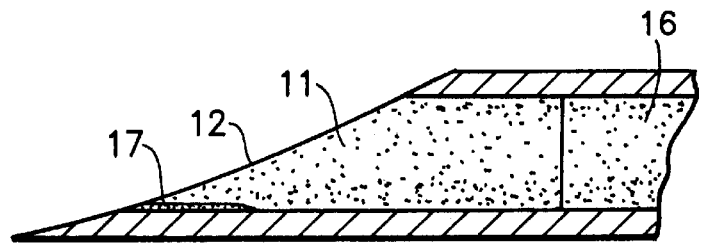
FIG. 5 is a side view of a cross section of the end of the preloaded device of FIG. 2 showing adhesive means for preventing the shaped implant from prematurely exiting the bore of the tubular member.
Figure 6:
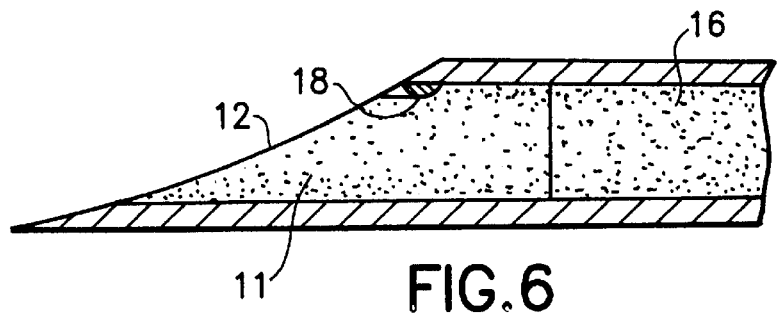
FIG. 6 shows an alternative means of retaining the shaped implant dosage form within the bore of the tubular member until such time the device is injected subcutaneously to deliver the implant dosage form(s).

When the implant device of the present invention is preloaded with one or more implant dosage form(s), means can be employed to keep the implant(s) in place within bore 2 of tubular member 1. FIGS. 5 and 6 show preferred embodiments of such means.

As shown in FIG. 5 an adhesive 17, preferably a soluble adhesive that is FDA approved for internal use, e.g. PVP, is employed to hold implant dosage form 11 within bore 2 of tubular member 1. The adhesive attachment should be readily overcome by downward force of plunger 6 when the device is used to inject the implant dosage form(s).

FIG. 6 shows an alternative means for keeping the implant dosage form(s) within bore 2 of tubular member 1. A boss 18 is provided on the inner wall of bore 2 of tubular member 1. Boss 18 contacts shaped implant dosage form 11 and provides sufficient resistance to keep the shaped implant dosage form 11 within bore 2 and in alignment with pointed elongated annular concavely beveled implanting end 3 thereby preventing it from being delivered until the device is used. The contact should be such as to be readily overcome by the downward force of plunger 6 when the device is used to inject the implant dosage form(s).

Other means for keeping the implant dosage form(s) in place within bore 2 of tubular member 1, until such time as the device is used, should be obvious to one skilled in the art. For example, a removable plastic tip can be fitted over the implanting end 3 of tubular member 1 so as to encase same and keep the implant dosage form(s) within bore 2. The tip can be removed immediately before the device is employed to inject the implant dosage form(s) contained therein.

The contents of all patents, patent applications, published articles, books, reference manuals and abstracts cited herein are hereby incorporated by reference in their entirety to more fully describe the state of the art to which the invention pertains.

As various changes can be made in the above-described subject matter without departing from the scope and spirit of the invention, it is intended that all subject matter contained in the above description, shown in the accompanying drawings, or defined in the appended claims, be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

What is claimed is:

1. A shaped solid implant dosage form comprising a cylindrical body having a substantially flat bottom and a top that angles downward from a first point at the top of the cylindrical body to a second point on the cylindrical body opposite the first point and closer to the bottom than the first point so that the top of the cylindrical body is truncated and has an ellipsoidal face.

2. An implant device comprising:
   (a) a tubular member having a central longitudinal axial bore therethrough, a pointed elongated annular concavely beveled implanting end and a charging end for inserting an implant dosage form in the bore;
   (b) a rod having an implanting end and at its opposite end a head, the head being affixed to the rod and having a diameter greater than that of the rod, the difference in the diameter of the head and the diameter of the rod defining a shoulder, the rod being removably insertable in the bore of the tubular member and slidably moveable therein along the longitudinal axis of the tubular member toward the implanting end for delivery of an implant dosage form contained in the bore; and
   (c) a stop member on the tubular member for hindering movement of the rod toward the implanting end sufficiently to prevent unintentional delivery of an implant dosage form when it is present within the bore but not sufficient to prevent such movement when the delivery is intended; the stop member being elastic and, prior to use of the device to deliver one or more implant dosage forms contained within the bore, being mounted in part on the rod and in part on the tubular member at the charging end of the tubular member so that the stop member simultaneously circumferentially contacts and encases a portion of the rod and a portion of the tubular member adjacent said portion of the rod.

3. The implant device as claimed in claim 2, wherein, after use of the device to deliver one or more implant dosage forms contained within the bore, the stop member is mounted on the tubular member, at the charging end, in direct contact with only the shoulder and the tubular member.

4. An implant device comprising:
   a) a tubular member having a central longitudinal axial bore therethrough, a pointed elongated annular concavely beveled implanting end and a charging end for inserting an implant dosage form in the bore;
   b) a rod having an implanting end and at its opposite end a head, the difference in the diameter of the head and the diameter of the rod defining a shoulder, the rod being removably insertable in the bore of the tubular member and slidably moveable therein along the longitudinal axis of the tubular member toward the implanting end for delivery of an implant dosage form contained in the bore;

c) a stop member on the tubular member for hindering movement of the rod toward the implanting end sufficiently to prevent unintentional delivery of an implant dosage form when it is present within the bore but not sufficient to prevent such movement when the delivery is intended; and d) at least one solid implant dosage form in said bore, the implant dosage form in the bore and adjacent to the implanting end having an ellipsoidal face that is in alignment with the pointed annular concavely beveled implanting end so as to present a complimentary substantially continuous ellipsoidal surface.

5. The device as claimed in claim 4, wherein the stop member is mounted at the charging end of the tubular member and in contact with the rod.

6. The device as claimed in claim 1, wherein the implant dosage form in the bore and adjacent to the implanting end has a cylindrical body having a substantially flat bottom and a top that angles downward from a first point at the top of the cylindrical body to a second point on the cylindrical body opposite to the first point and closer to the bottom than the first point so that the top of the cylindrical body is truncated whereby said ellipsoidal face is produced.

7. The device as claimed in claim 4, wherein prior to use of the device to deliver one or more implant dosage forms contained within the bore, the stop member is mounted in part on the rod and in part on the tubular member at the charging end.

8. The device as claimed in claim 4, wherein, after use of the device to deliver one or more implant dosage forms contained within the bore, the stop member is mounted on the tubular member at the charging end and in contact with the shoulder.

9. The device as claimed in claim 4, wherein the stop means is frictionally mounted on the tubular member and when sufficient force is applied to the head of the rod to overcome frictional resistance of the stop member and move the rod in the bore toward the implanting end a sufficient distance to eject an implant dosage form from the bore, is moveable from a first position at which the stop member is mounted partly on the tubular member at the charging end and partly on the rod to a second position at which the stop member is mounted on the tubular member at the charging end and in contact with the shoulder.

10. The device as claimed in claim 4, further including means for preventing the implant dosage form charged within the bore from exiting the bore prior to use of the device.

11. The device as claimed in claim 10, wherein the means for preventing comprises an adhesive in the bore and in contact with the implant dosage form and the bore wall at the implanting end.

12. The device as claimed in claim 10, wherein the means for preventing comprises a boss on the wall of the bore adjacent the implanting end and in contact with the implant dosage form at the implanting end.

* * * * *